US007994298B2

(12) United States Patent
Zhang et al.

(10) Patent No.: US 7,994,298 B2
(45) Date of Patent: *Aug. 9, 2011

(54) CHIMERIC NK RECEPTOR AND METHODS FOR TREATING CANCER

(75) Inventors: Tong Zhang, Lebanon, NH (US); Charles L. Sentman, West Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 984 days.

This patent is subject to a terminal disclaimer.

(21) Appl. No.: 11/575,878

(22) PCT Filed: Aug. 31, 2005

(86) PCT No.: PCT/US2005/031100
§ 371 (c)(1),
(2), (4) Date: Apr. 19, 2007

(87) PCT Pub. No.: WO2006/036445
PCT Pub. Date: Apr. 6, 2006

(65) Prior Publication Data
US 2010/0029749 A1 Feb. 4, 2010

Related U.S. Application Data

(60) Provisional application No. 60/681,782, filed on May 17, 2005, provisional application No. 60/612,836, filed on Sep. 24, 2004.

(51) Int. Cl.
*C12N 15/11* (2006.01)
*C12N 15/63* (2006.01)
*C12N 15/85* (2006.01)

(52) U.S. Cl. ..................... 536/23.1; 435/320.1; 435/325

(58) Field of Classification Search .................. 536/23.1; 435/320.1, 325
See application file for complete search history.

(56) References Cited

U.S. PATENT DOCUMENTS 5,359,046 A 10/1994 Capon et al.
6,407,319 B1 6/2002 Rose-Fricker et al.

FOREIGN PATENT DOCUMENTS
WO  WO02068615 A2  9/2002

OTHER PUBLICATIONS

Wu et al (Science 285: 730-732, 1999).*
Heuser et al, Gene Therapy, 10:1408-1419, 2003).*
Diefenbach et al (Current Opinion in Immunology, 15(1): 37-44, 2003).*
Cambier et al (The Journal of Immunology, 3281-3285, 1995).*
Wilson et al (Immunologic Research, 22/1:21-42,2 000).*
Rosen et al (J Immunol, 173; 2470-2478, 2004).*

Baba et al., "N-Linked Carbohydrate on Human Leukocyte Antigen-C and Recognition by natural Killer Cell Inhibitory Receptors", Human Immunology 20000 61:1202-1218.
Bonini et al., "HSV-TK Gene Transfer into Donor Lymphocytes for Control of Allogeneic Graft-Versus-Leukemia", Science 1997 276:1720-1724.
Clay et al., "Efficient Transfer of a Tumor Antigen-Reactive TCR to Human Peripheral Blood Lymphocytes Confers Anti-Tumor Reactivity", The Journal of Immunology 1999 163:507-513.
Gonzalez et al., "Genetic engineering of cytolytic T lymphocytes for adoptive T-cell therapy of neuroblastoma", J Gene Med 2004 6:704-711.
Moingeon et al., "Human natural killer cells and mature T lymphocytes express identical CD3 Zeta subunits as defined by cDNA cloning and sequence analysis", Eur. J. Immunol. 1990 20:1741-1745.
Oelke et al., "Ex vivo induction and expansion of antigen-specific cytotoxic T cells by HLA-Ig-coated artificial antigen-presenting cells", Nature Medicine 2003 9(5):619-624.
Reilly, R. Todd, "Proper Costimulation of Tumor-Reactive T Lymphocytes May Provide a Key to Unlock Their Antitumor Activity", Cancer Biology & Therapy 2003 2(5):587-588.
Stancovski et al., "Targeting of T Lymphocytes to Neu/HER2-Expressing Cells Using Chimeric Single Chain Fv Receptors", J. Immunol 1993 151(11):6577-6582.
Stevens et al., "Generation of Tumor-Specific CTLs from Melanoma Patients by Using Peripheral Blood Stimulated with Allogeneic Melanoma Tumor Cell Lines", J. Immunol 1995 154:762-771.
Thomis et al., "A Fas-based suicide switch in human T cells for the treatment of graft-versus-host disease", Blood 2001 97(5):1249-1257.
Zhang et al., "Chimeric NK-receptor-bearing T cells mediate antitumor immunotherapy", Blood 2005 106(5):1544-1551.
NCBI Accession No. NM_002262 [gi:7669497] with Revision History—Feb. 5, 2006—Nov. 17, 2006.
NCBI Accession No. NM_007334 [gi:7669498] with Revision History—Feb. 5, 2006—Nov. 17, 2006.
NCBI Accession No. NM_002543 [gi:37595562] with Revision History—Aug. 13, 2006—Feb. 18, 2007.
NCBI Accession No. AF461811 [gi:18182679] Jan. 17, 2002.
NCBi Accession No. AJ312373 [gi:14599393] with Revision History—Jul. 3, 2001-Apr. 15, 2005.
NCBI Accession No. NM_001781 [gi: 4502680] with Revision History—Mar. 30, 2006-Nov. 17, 2006.
NCBI Accession No. U11276 [gi:538270] with Revision History-Sep. 16, 1994-Sep. 23. 1994.
NCBI Accession No. AF098358 [gi:4139191].
NCBI Accession No. AF133299 [gi:6651064].
NCBI Accession No. NM_016509 with Revision History—Mar. 2, 2006-Nov. 18, 2006.
NCBI Accession No. BC-30937 {gi:24980984] with Revision History—Jun. 25, 2004-Jul. 15, 2006.

(Continued)

*Primary Examiner* — Thaian N Ton
*Assistant Examiner* — Magdalene Sgagias
(74) *Attorney, Agent, or Firm* — Hunton & Williams LLP

(57) ABSTRACT

The present invention relates to chimeric immune receptor molecules for reducing or eliminating tumors. The chimeric receptors are composed a C-type lectin-like natural killer cell receptor, or a protein associated therewith, fused to an immune signaling receptor containing an immunoreceptor tyrosine-based activation motif. Methods for using the chimeric receptors are further provided.

4 Claims, 1 Drawing Sheet

OTHER PUBLICATIONS

NCBI Accession No. AF072845 [gi:5690195].
NCBI Accession No. AF461157 [gi:18182677].
NCBI Accession No. AF461812 [gi:18182681].
NCBI Accession No. NM_198053 [gi:37595564] with Revision History—Oct. 15, 2006-Jan. 14, 2007.
NCBI Accession No. AJ271694 [gi:6900101] with Revision History—Feb. 2, 2000-Nov. 14, 2006.
NCBI Accession No. AJ001383 [gi:3647278] with Revision History—Sep. 22, 1998.
NCBI Accession No. AB055881 [gi:17221621] with Revision History—Dec. 1, 2001.
NCBI Accession No. AJ225109 [gi:4493701] with Revision History—Mar. 15, 1999.
NCBI Accession No. AF019562 [gi:2905993] with Revision History—Jan. 26, 1999.
NCBI Accession No. M33195 [gi:182487] with Revision History—Oct. 2, 1992-Apr. 27, 1993.
NCBI Accession No. NM_016523 [gi:7705573] with Revision History—Apr. 22, 2005-Feb. 27, 2007.
NCBI Accession No. AJ001684 [gi:2980858] with Revision History—Sep. 4, 1998-Nov. 14, 2006.
NCBI Accession No. NM_001782 [gi:4502682] with Revision History—Aug. 13, 2006-Mar. 11, 2007.
Wu et al., An activating immunoreceptor complex formed by NKG2D and DAP10, Science, 285: 730-732, 1999.
Heuser et al., T-cell activation by recombinant immunoreceptors: impact of the intracellular signalling domain on the stability of receptor expression and antigen-specific activation of grafted T-cells, Gene Therapy 10: 1408-1419, 2003.
Diefenbach et al., Innate immune recognition by stimulatory immunoreceptors, Current Opinion in Immunology, 15(1): 37-44, 2003.
Belakova et al., DNA vaccines: are they still just a powerful tool for the future? Arch Immunol Ther Exp. (Warsz), 55(6): 387-398, 2007.
Mittendorf et al., Breast cancer vaccines: promise for the future or pipe dream? Cancer, 110(8): 1677-1686, 2007.
Ulmer et al., Gene-based vaccines: recent technical and clinical advances. Trends Mol Med. 12(5): 216-222, 2006.
Diefenbach et al., The innate immune response to tumors and its role in the induction of T-cell immunity, Immunol Rev. 188: 9-21, 2002.
Gilham et al., Primary polyclonal human T lymphocytes targeted to carcino-embryonic antigens and neural cell adhesion molecule tumor antigens by CD3zeta-based chimeric immune receptors, J. Immunother, Mar.-Apr. 2002: 25(2): 139-151, 2002.
Lowin-Kropf et al., Cytoskeletal polarization of T cells is regulated by an immunoreceptor tyrosine-based activation motif-dependent mechanism, J Cell Biol. 140(40: 861-871, 1998.
Bauer et al., Activation of NK cells and T cells by NKG2D, a receptor for stress-inducible MICA, Science 285(5428): 727-729, 1999.
Houchins et al., DNA sequence analysis of NKG2, a family of related cDNA clones encoding type II integral membrane proteins on human natural killer Glees, J Exp. Med. 173(4): 1017-1020, 1991.

* cited by examiner

CHIMERIC NK RECEPTOR AND METHODS FOR TREATING CANCER

This application claims the benefit of priority from U.S. provisional patent application Ser. Nos. 60/612,836, filed Sep. 24, 2004 and 60/681,782, filed May 17, 2005, whose contents are incorporated herein by reference in their entireties.

INTRODUCTION

This invention was made in the course of research sponsored by the National Cancer Institute (Grant No. CA 101748). The U.S. government may have certain rights in this invention.

BACKGROUND OF THE INVENTION

T cells, especially cytotoxic T cells, play important roles in anti-tumor immunity (Rossing and Brenner (2004) *Mol. Ther.* 10:5-18). Adoptive transfer of tumor-specific T cells into patients provides a means to treat cancer (Sadelain, et al. (2003) *Nat. Rev. Cancer* 3:35-45). However, the traditional approaches for obtaining large numbers of tumor-specific T cells are time-consuming, laborious and sometimes difficult because the average frequency of antigen-specific T cells in periphery is extremely low (Rosenberg (2001) *Nature* 411: 380-384; Ho, et al. (2003) *Cancer Cell* 3:431-437; Crowley, et al. (1990) *Cancer Res.* 50:492-498). In addition, isolation and expansion of T cells that retain their antigen specificity and function can also be a challenging task (Sadelain, et al. (2003) supra). Genetic modification of primary T cells with tumor-specific immunoreceptors, such as full-length T cell receptors or chimeric T cell receptor molecules can be used for redirecting T cells against tumor cells (Stevens, et al. (1995) *J. Immunol.* 154:762-771; Oelke, et al. (2003) *Nat. Med.* 9:619-624; Stancovski, et al. (1993) *J. Immunol.* 151:6577-6582; Clay, et al. (1999) *J. Immunol.* 163:507-153). This strategy avoids the limitation of low frequency of antigen-specific T cells, allowing for facilitated expansion of tumor-specific T cells to therapeutic doses.

Natural killer (NK) cells are innate effector cells serving as a first line of defense against certain viral infections and tumors (Biron, et al. (1999) *Annu. Rev. Immunol.* 17:189-220; Trinchieri (1989) *Adv. Immunol.* 47:187-376). They have also been implicated in the rejection of allogeneic bone marrow transplants (Lanier (1995) *Curr. Opin. Immunol.* 7:626-631; Yu, et al. (1992) *Annu. Rev. Immunol.* 10:189-214). Innate effector cells recognize and eliminate their targets with fast kinetics, without prior sensitization. Therefore, NK cells need to sense if cells are transformed, infected, or stressed to discriminate between abnormal and healthy tissues. According to the missing self phenomenon (Kärre, et al. (1986) *Nature (London)* 319:675-678), NK cells accomplish this by looking for and eliminating cells with aberrant major histocompatibility complex (MHC) class I expression; a concept validated by showing that NK cells are responsible for the rejection of the MHC class I-deficient lymphoma cell line RMA-S, but not its parental MHC class I-positive line RMA.

Inhibitory receptors specific for MHC class I molecules have been identified in mice and humans. The human killer cell Ig-like receptors (KIR) recognize HLA-A, -B, or -C; the murine Ly49 receptors recognize H-2K or H-2D; and the mouse and human CD94/NKG2 receptors are specific for $Qa1^b$ or HLA-E, respectively (Long (1999) *Annu. Rev. Immunol.* 17:875-904; Lanier (1998) *Annu. Rev. Immunol.* 16:359-393; Vance, et al. (1998) *J. Exp. Med.* 188:1841-1848).

Activating NK cell receptors specific for classic MHC class I molecules, nonclassic MHC class I molecules or MHC class I-related molecules have been described (Bakker, et al. (2000) *Hum. Immunol.* 61:18-27). One such receptor is NKG2D (natural killer cell group 2D) which is a C-type lectin-like receptor expressed on NK cells, γδ-TcR⁺ T cells, and CD8⁺ αβ-TcR⁺ T cells (Bauer, et al. (1999) *Science* 285:727-730). NKG2D is associated with the transmembrane adapter protein DAP10 (Wu, et al. (1999) *Science* 285:730-732), whose cytoplasmic domain binds to the p85 subunit of the PI-3 kinase.

In humans, two families of ligands for NKG2D have been described (Bahram (2000) *Adv. Immunol.* 76:1-60; Cerwenka and Lanier (2001) *Immunol. Rev.* 181:158-169). NKG2D binds to the polymorphic MHC class I chain-related molecules (MIC)-A and MICB (Bauer, et al. (1999) supra). These are expressed on many human tumor cell lines, on several freshly isolated tumor specimens, and at low levels on gut epithelium (Groh, et al. (1999) *Proc. Natl. Acad. Sci. USA* 96:6879-6884). NKG2D also binds to another family of ligands designated the UL binding proteins (ULBP)-1, -2, and -3 molecules (Cosman, et al. (2001) *Immunity* 14:123-133; Kubin, et al. (2001) *Eur. J. Immunol.* 31:1428-1437). Although similar to class I MHC molecules in their α1 and α2 domains, the genes encoding these proteins are not localized within the MHC. Like MIC (Groh, et al. (1996) supra), the ULBP molecules do not associate with $β_2$-microglobulin or bind peptides. The known murine NKG2D-binding repertoire encompasses the retinoic acid early inducible-1 gene products (RAE-1) and the related H60 minor histocompatibility antigen (Cerwenka, et al. (2000) *Immunity* 12:721-727; Diefenbach, et al. (2000) *Nat. Immunol.* 1:119-126). RAE-1 and H60 were identified as ligands for mouse NKG2D by expression cloning these cDNA from a mouse transformed lung cell line (Cerwenka, et al. (2000) supra). Transcripts of RAE-1 are rare in adult tissues but abundant in the embryo and on many mouse tumor cell lines, indicating that these are oncofetal antigens.

Recombinant receptors containing an intracellular domain for activating T cells and an extracellular antigen-binding domain, which is typically a single-chain fragment of a monoclonal antibody and is specific for a tumor-specific antigen, are known in the art for targeting tumors for destruction. See, e.g., U.S. Pat. No. 6,410,319.

Baba et al. ((2000) *Hum. Immunol.* 61:1202-18) teach KIR2DL1-CD3 zeta chain chimeric proteins. Further, WO 02/068615 suggests fusion proteins of NKG2D containing the external domain of NKG2D with a distinct DAP10 interacting domain or with cytoplasmic domains derived from other signaling molecules, for example CD28, for use in engineering cells that respond to NKG2D ligands and potentially create a system with enhanced signaling capabilities.

U.S. Pat. No. 5,359,046 discloses a chimeric DNA sequence encoding a membrane bound protein, wherein the chimeric DNA comprises a DNA sequence encoding a signal sequence which directs the membrane bound protein to the surface membrane; a DNA sequence encoding a non-MHC restricted extracellular binding domain of a surface membrane protein selected from the group consisting of CD4, CD8, IgG and single-chain antibody that binds specifically to at least one ligand, wherein said ligand is a protein on the surface of a cell or a viral protein; a transmembrane domain from a protein selected from the group consisting of CD4, CD8, IgG, single-chain antibody, the CD3 zeta chain, the CD3 gamma chain, the CD3 delta chain and the CD3 epsilon chain; and a cytoplasmic signal-transducing domain of a protein that activates an intracellular messenger system selected from the group consisting of the CD3 zeta chain, the CD3 gamma chain, the CD3 delta chain and the CD3 epsilon chain, wherein the extracellular domain and cytoplasmic domain are not naturally joined together and the cytoplasmic domain is not naturally joined to an extracellular ligand-binding domain, and when the chimeric DNA is expressed as a membrane bound protein in a selected host cell under conditions suitable for expression, the membrane bound protein initiates signaling in the host cell.

SUMMARY OF THE INVENTION

The present invention is a nucleic acid construct for expressing a chimeric receptor to reduce or eliminate a tumor. The nucleic acid construct contains a first nucleic acid sequence encoding a promoter operably linked to a second nucleic acid sequence encoding a chimeric receptor protein comprising a C-type lectin-like natural killer cell receptor, or a protein associated therewith, fused to an immune signaling receptor having an immunoreceptor tyrosine-based activation motif of SEQ ID NO:1. In one embodiment, the nucleic acid construct is in a vector. In particular embodiments, the nucleic acid construct further contains a suicide gene.

The present invention also relates to a method for reducing or eliminating tumors. The method involves introducing into an isolated T cell of a patient having or suspected of having a tumor a nucleic acid construct containing a first nucleic acid sequence encoding a promoter operably linked to a second nucleic acid sequence encoding a chimeric receptor protein comprising a C-type lectin-like natural killer cell receptor, or a protein associated therewith, fused to an immune signaling receptor having an immunoreceptor tyrosine-based activation motif of SEQ ID NO:1. The T cell is subsequently injected back into the patient so that the chimeric receptor is expressed on the surface of the T cell to activate anti-tumor immunity in the patent thereby reducing or eliminating the tumor.

DETAILED DESCRIPTION OF THE INVENTION

Figure 1:
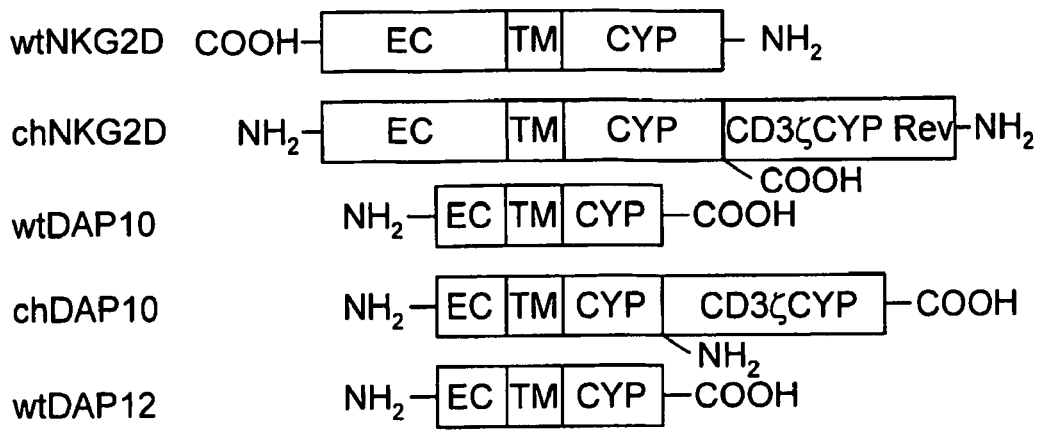
FIG. 1 illustrates chimeric NK receptors exemplified herein. Extracellular (EC), transmembrane (TM), and cytoplasmic (Cyp) portions are indicated. Wild-type (WT) and chimeric (CH) forms of the receptors are indicated, wherein $NH_2$ denotes the N-terminus and COOH denotes the C-terminus.

The present invention relates to a chimeric receptor molecule composed of a natural killer cell receptor and an immune signaling receptor expressed on the surface of a T cell to activate killing of a tumor cell. Nucleic acid sequences encoding the chimeric receptor molecule are introduced into a patient's T-cells ex vivo and T-cells that express the chimeric receptor molecule are subsequently injected back into the patient. In this manner, the chimeric receptor molecules provide a means for the patient's own immune cells to recognize and activate anti-tumor immunity and establish long-term, specific, anti-tumor responses for treating tumors or preventing regrowth of dormant or residual tumor cells. To prevent potential side effects that may occur from uncontrolled inflammation or response against non-tumor tissue, suicide genes are further introduced into the T-cells expressing the chimeric receptor molecule. The suicide gene is activated by administering an agent, specific for the suicide gene, to the patient thereby eliminating all cells expressing the chimeric receptor molecule.

By way of illustration, murine chimeric receptor molecules composed of NKG2D or Dap10 in combination with a N-terminally attached CD3ζ were generated and expressed in murine T-cells. NKG2D is a type II protein, in which the N-terminus is located intracellularly (Raulet (2003) Nat. Rev. Immunol. 3:781-790), whereas the CD3ζ chain is type I protein with the C-terminus in the cytoplasm (Weissman, et al. (1988) Proc. Natl. Acad. Sci. USA 85:9709-9713). To generate a chimeric NKG2D-CD3ζ fusion protein, an initiation codon ATG was placed ahead of the coding sequence for the cytoplasmic region of the CD3ζ chain (without a stop codon TAA) followed by a wild-type NKG2D gene. Upon expression, the orientation of the CD3ζ portion is reversed inside the cells. The extracellular and transmembrane domains are derived from NKG2D. A second chimeric gene encoding the Dap10 gene followed by a fragment coding for the CD3ζ cytoplasmic domain was also constructed. The structures of the chimeric and wild-type receptors used are diagrammed in FIG. 1.

To determine whether murine chimeric NKG2D or murine chimeric Dap10 receptors could be expressed in a similar manner as wild-type murine NKG2D or Dap10, a NKG2D gene with an adaptor protein gene (Dap10/Dap12) were co-transfected into Bosc23 cells and NKG2D expression was determined by flow cytometry. To analyze those cells that were transfected, a bicistronic vector with a green fluorescent protein (GFP) gene controlled by an internal ribosome entry site (IRES) was used. NKG2D surface expression was normalized by gating on the GFP$^+$ cell population. Like many NK receptors, such as CD94/NKG2C, Ly49D, and Ly49H, NKG2D needs to be associated with adaptor proteins (i.e., Dap10 and/or Dap12) for surface expression (Raulet (2003) supra; Lanier (2003) Curr. Opin. Immunol. 15:308-314). Packaging cell Bosc23 did not express either NKG2D or Dap10/Dap12, and transfection with only one of the two components did not give rise to surface expression of NKG2D. However, co-transfection of a NKG2D gene along with an adaptor protein gene led to significant membrane expression of NKG2D. Compared with Dap12, Dap10 transfection resulted in higher NKG2D surface expression. Surface expression of NKG2D after association with chimeric Dap10 adaptor was higher than that with wild-type DAP10. Higher surface expression of NKG2D was also observed after transfection with chimeric NKG2D than with wild-type NKG2D genes, especially when pairing with the Dap12 gene (>5-fold increase in MFI).

Concentrated, high-titer, retroviral vectors (ecotropic) were used to infect C57BL/6 spleen cells, and NKG2D surface expression was determined by flow cytometry seven days after retroviral transduction. Genetic modification of T cells with wild-type Dap10, Dap12 and NKG2D did not significantly increase the surface expression of NKG2D (10-20%) compared to vector alone. In contrast, significantly higher NKG2D expression was observed in T cells modified with either chimeric NKG2D (42%) or chimeric Dap10

(64%). In chimeric Dap10-transduced T cells, the surface-expressed NKG2D molecules were only due to endogenous molecules, whereas both endogenous and exogenous NKG2D molecules were responsible for surface expression in chimeric NKG2D-modified T cells. Taken together, these data indicate that chimeric NKG2D and chimeric Dap10 molecules are expressed in a similar manner as the wild-type molecules and that they increase NKG2D expression on T cells.

To assess whether the murine chimeric DAP10 or murine chimeric NKG2D-transduced T cells were capable of recognizing NKG2D ligands, NKG2D ligand-positive tumor cells (RMA/Rae-1β, RMA/H60 and YAC-1) were used as targets for chimeric NKG2D-bearing T cells. Chimeric DAP10 or chimeric NKG2D-transduced T cells produced high amounts of IFN-γ (20-30 ng/mL) after co-culture with RMA/Rae-1β, RMA/H60 or YAC-1 cells (Table 1) but not with RMA cells (no ligands), indicating that these chimeric NKG2D-modified T cells could functionally recognize NKG2D ligand-bearing tumor cells.

as well as Th1 cytokines, GM-CSF and IL-3, but not Th2 cytokines IL-5 and IL-10. In contrast, wild-type Dap10, Dap12 or NKG2D alone-modified T cells did not show any significant response to the stimulation by RMA/Rae-1β, RMA/H60 or YAC-1 cells. These data demonstrate that the chimeric molecules led to the direct activation of T cells.

Figure 2:
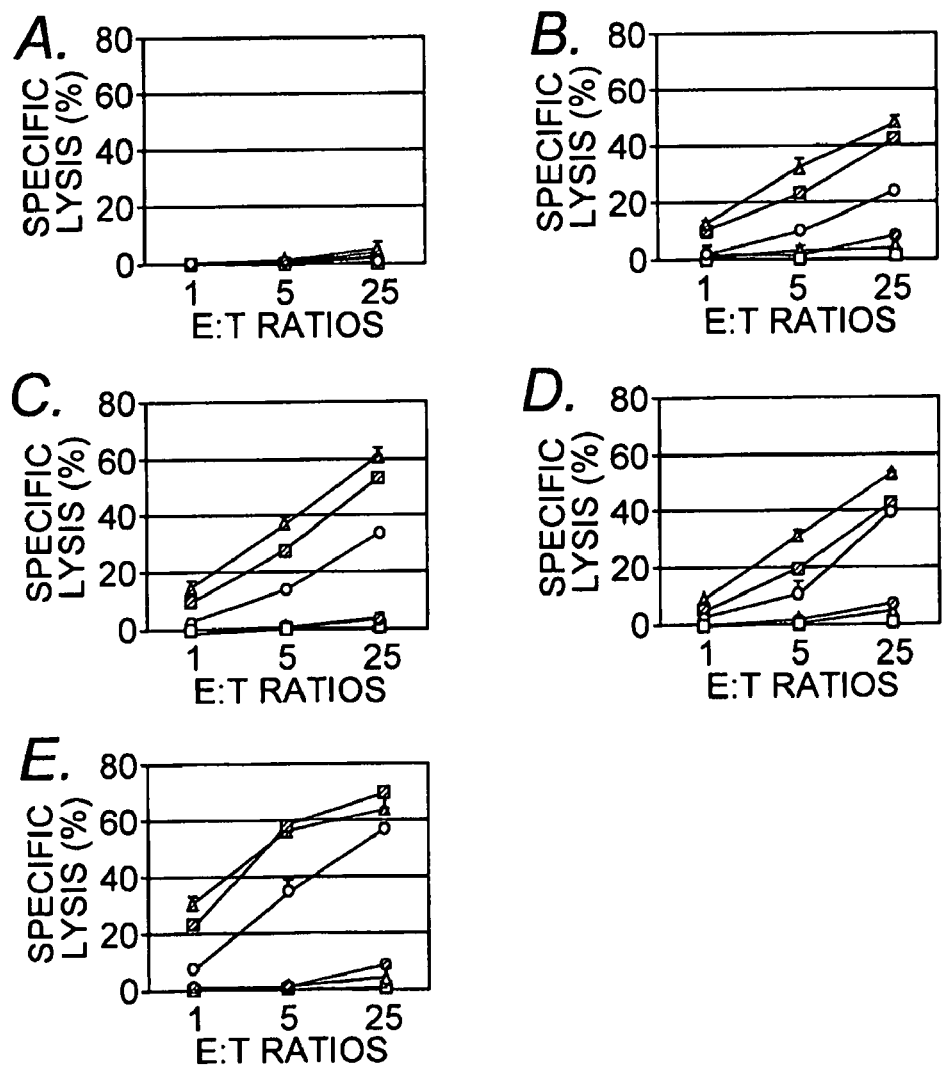
FIG. 2 shows specific lysis of target cells by gene-modified primary T cells. Effector T cells modified with vector only (shaded diamond), wild-type NKG2D (open square), murine chimeric NKG2D (shaded square), wild-type DAP10 (open triangle), murine chimeric DAP10 (shaded triangle), or wild-type DAP12 (open circle) were co-cultured with target cells RMA (Panel A), RMA/Rae-1β (Panel B), RMA/H60 (Panel C), YAC-1 (Panel D), or EG7 (Panel E) cells, respectively, at ratios from 1:1 to 25:1 in a 4 hour $^{51}Cr$ release assay. The data are presented as mean±SD and representative of 3 to 5 independent experiments.

The cytotoxic activity of murine chimeric NKG2D-modified splenic T cells against tumor cells was also determined. Chimeric Dap10 or chimeric NKG2D-transduced T cells were able to lyse NKG2D ligand-expressing target cells (RMA/Rae-1β, RMA/H60, EG7 and YAC-1) in vitro (FIG. 2, Panels B-E). The specificity of the interaction was apparent from the absence of lysis of YAC-1, EG7, RMA/Rae-1β and RMA/H60 cells by vector only-transduced T cells, and the lack of lysis of RMA cells by chimeric Dap10 or chimeric NKG2D-modified T cells (FIG. 2, Panel A). Similar to cytokine production, no significant specific lysis of tumor cells was observed by wild-type Dap10 or wild-type NKG2D-modified T cells. T cells transduced with wild-type Dap12 were able to kill target cells that expressed ligands for NKG2D. Activated

TABLE 1

| | IFN-γ (ng/mL ± SD) | | | | |
| --- | --- | --- | --- | --- | --- |
| Construct | Media | RMA | RMA/Rae-1β | RMA/H60 | YAC-1 |
| Vector Only | 0.03 ± 0.03 | 0.09 ± 0.18 | 0.02 ± 0.03 | 0.11 ± 0.63 | 0.84 ± 0.29 |
| Wild-type NKG2D* | 0.01 ± 0.01 | 0.10 ± 0.21 | 0.04 ± 0.06 | 0.05 ± 0.00 | 1.08 ± 1.48 |
| Chimeric NKG2D | 0.07 ± 0.08 | 0.37 ± 0.34 | 4.70 ± 0.78 | 8.40 ± 1.60 | 17.80 ± 4.60 |
| Wild-type DAP10* | 0.01 ± 0.10 | 0.11 ± 0.11 | 0.04 ± 0.03 | 0.09 ± 0.03 | 1.43 ± 1.72 |
| Chimeric DAP10 | 0.49 ± 0.55 | 0.82 ± 0.52 | 7.50 ± 4.40 | 18.60 ± 7.60 | 28.70 ± 8.30 |
| Wild-Type DAP12# | 0.00 ± 0.01 | 0.00 ± 0.01 | 0.53 ± 0.67 | 0.13 ± 0.10 | 0.73 ± 0.09 |

*p = 0.74;
p = 0.56.
Data are representative of 3 experiments.

Similarly, chimeric human NKG2D-bearing CD8+ T cells secrete IFN-γ when brought into contact with human tumor cells from breast cancer (MCF-7, T47D), prostate cancer (DU145), pancreatic cancer (Pan-1), and melanoma cancer (A375) (Table 2). T cells were cultured with irradiated tumor cells at a 4:1 ratio for 72 hours and IFN-γ was measured by ELISA. T cells cultured without tumor cells functioned as a media only control which produced no detectable IFN-γ. The specificity of the interaction was evident by comparing chimeric NKG2D transduced T cells to vector only.

TABLE 2

| | IFN-γ (pg/mL ± SD) | | | | |
| --- | --- | --- | --- | --- | --- |
| Construct | T47D | MCF-7 | Panc-1 | DU-145 | A375 |
| Vector Only | 28.9 (±12.5) | 53.5 (±3.6) | 97.2 (±8.0) | 61.4 (±4.2) | 262.4 (±44.2) |
| Wild-type NKG2D* | 35.2 (±30.0) | 43.6 (±9.2) | 115.8 (±89.8) | 84.4 (±47.1) | 200.5 (±79.5) |
| Chimeric NKG2D | 130.3 (±70.4) | 2928.3 (±251.1) | 5028.1 (±407.2) | 4427.9 (±470.1) | 2609.2 (±293.2) |
| Tumor Alone | 23.4 (±26.9) | 17.7 (±8.7) | 26.6 (±7.5) | 27.4 (±10.2) | 11.4 (±17.7) |

In addition, upon NKG2D ligation, chimeric DAP10 or chimeric NKG2D-modified T cells also released significant amounts of proinflammatory chemokines (CCL3 and CCL5), murine CD8+ T cells express NKG2D (associated with Dap10), so expression of Dap12 would allow the endogenous NKG2D to associate with Dap12 and provide a primary activation signal. It is noteworthy that T cells transduced with Dap12 were three- to five-fold less efficient than T cells transduced with chimeric NK receptors at killing tumor cells. The killing of YAC-1 and EG7 tumor cells demonstrates that chimeric NK receptors provide the T cells with a means to kill tumor cells that express endogenous NKG2D ligands.

These data demonstrated the need for NKG2D ligand expression on the target cells. To investigate the role of the NKG2D receptor, it was determined whether blocking antibodies to NKG2D would diminish cytotoxic activity. Chimeric NKG2D-transduced T cells killed RMA/Rae-1β, and EG7 tumor cells and this activity was reduced when anti-NKG2D antibodies were included in the assay. Vector only-transduced T cells were unable to kill the target cells and the activity was not changed with the addition of anti-NKG2D antibodies. While the data indicate that the NKG2D receptor was responsible for the activity in these assays, the chimeric receptors may have, in some way, altered the T cells to kill via their T cell receptor. To address this, the ability of chimeric NKG2D-transduced T cells to kill RMA/Rae-1β tumor cells was examined. RMA-S cells are deficient in TAP genes and express very low levels of MHC class I molecules on the cell surface and no MHC class II molecules (Aldrich, et al. (1992) J. Immunol. 149:3773-3777). Chimeric NKG2D-bearing T cells killed RMA/Rae-1β tumor cells but not RMA-S cells. Vector-transduced T cells did not kill either RMA-S cell line. Thus, these data indicate that chimeric NKG2D functions via direct NKG2D recognition of its ligand on target cells.

Having shown that chNKG2D-modified T cells could react against NKG2D ligand-positive tumor cells in vitro, the therapeutic potential of chimeric NKG2D-modified T lymphocytes was determined in vivo. Chimeric NKG2D-bearing T cells ($10^6$) were co-injected with RMA/Rae-1β tumor cells ($10^5$) subcutaneously to C57BL/6 mice. T cells transduced with the chimeric NKG2D construct significantly ($P<0.05$ at days 5-15) inhibited the growth of RMA/Rae-1β tumors compared with vector-transduced T cells or tumor alone (Table 3). Approximately 36% (4/11) of chimeric NKG2D-bearing T cell-treated mice were tumor-free after 30 days. Chimeric NKG2D-bearing T cells did not show any significant inhibition effects on the growth of wild-type RMA cells, indicating that inhibition of RMA/Rae-1β tumor growth by chimeric NKG2D T cells was mediated by chimeric NKG2D-Rae-1β engagement.

TABLE 3

| | Tumor Area (Mean mm² ± SEM) | | |
|---|---|---|---|
| Day | T Cells transduced with chimeric NKG2D + RMA/Rae-1β | T cells transduced with vector only + RMA/Rae-1β | RMA/Rae-1β |
| 0 | 0.00 ± 0.00 | 0.00 ± 0.00 | 0.00 ± 0.00 |
| 5 | 0.00 ± 0.00 | 16.14 ± 2.86 | 6.79 ± 1.47 |
| 7 | 3.10 ± 1.40 | 38.45 ± 3.79 | 28.69 ± 5.49 |
| 9 | 8.11 ± 3.09 | 57.40 ± 6.43 | 42.22 ± 6.38 |
| 11 | 11.84 ± 5.24 | 90.31 ± 11.64 | 60.60 ± 12.10 |
| 13 | 14.73 ± 7.24 | 127.30 ± 16.85 | 82.67 ± 19.44 |
| 15 | 20.60 ± 8.32 | N.D. | 110.51 ± 29.07 |

Results are a summary of three experiments.

In a second and more stringent model, transduced T cells ($10^7$) were adoptively transferred i.v. into B6 mice one day before s.c. tumor inoculation in the right flank. These chimeric NKG2D-bearing T cells significantly ($P<0.05$ at days 9-17) suppressed the growth of RMA/Rae-1β tumors (s.c.) compared with control vector-modified T cells (Table 4). As for the toxicity of treatment with chimeric NKG2D-modified T cells, the animals treated with chimeric NKG2D-bearing T cells did not show any overt evidence of inflammatory damage (i.e., ruffled hair, hunchback or diarrhea, etc.) indicating there was no overt toxicity.

TABLE 4

| | Tumor Area (Mean mm² ± SEM) | |
|---|---|---|
| Day | T Cells transduced with chimeric NKG2D | Control T cells with Vector Only |
| 5 | 3.06 ± 1.97 | 4.41 ± 2.20 |
| 7 | 12.14 ± 3.06 | 17.81 ± 1.75 |
| 9 | 13.94 ± 2.85 | 30.58 ± 3.87 |
| 11 | 25.92 ± 4.77 | 45.13 ± 3.27 |
| 13 | 32.11 ± 5.84 | 64.83 ± 10.45 |
| 15 | 34.39 ± 9.77 | 80.72 ± 13.34 |
| 17 | 37.81 ± 11.68 | 96.30 ± 14.15 |

Results are a summary of three experiments.

Because the immune system can select for tumor variants, the most effective immunotherapies for cancer are likely going to be those that induce immunity against multiple tumor antigens. Thus, it was tested whether treatment with chimeric NKG2D-bearing T cells could induce host immunity against wild-type tumor cells. Mice that were treated with chimeric NKG2D-bearing T cells and RMA/Rae-1β tumor cells, and were tumor-free after 30 days, were challenged with RMA tumor cells. These tumor-free mice were resistant to a subsequent challenge of wild-type RMA cells ($10^4$), whereas all control naïve mice had aggressive tumors (tumor area: ~100 mm²) after 2 weeks (Table 5). This observation indicates that adoptive transfer of chimeric NKG2D-bearing T cells allows hosts to generate T cell memory.

TABLE 5

| | Tumor Area (Mean mm² ± SEM) | |
|---|---|---|
| Day | Mice treated with T Cells transduced with chimeric NKG2D + RMA/Rae-1β | Näive Mice |
| 5 | 0.00 ± 0.00 | 1.33 ± 2.31 |
| 7 | 0.00 ± 0.00 | 11.65 ± 10.20 |
| 9 | 0.00 ± 0.00 | 38.75 ± 8.84 |
| 11 | 0.00 ± 0.00 | 60.17 ± 6.10 |
| 13 | 0.00 ± 0.00 | 91.10 ± 5.59 |
| 15 | 0.00 ± 0.00 | 102.81 ± 17.94 |
| 19 | 0.00 ± 0.00 | 146.71 ± 45.72 |

Results are a summary of three experiments.

In similar experiments, human chimeric receptor molecules composed of NKG2D or Dap10 in combination with a N-terminally attached CD3ζ were generated and expressed in Bosc23 cells. Surface expression of NKG2D was not observed when either human Dap10 or human chimeric NKG2D were transfected alone. However, co-transfection of a human chimeric NKG2D or human chimeric NKG2D-GFP gene along with a wild-type human DAP10 gene or mouse DAP10-GFP construct led to significant membrane expression of NKG2D.

Binding of a human NKG2D fusion protein, composed of NKG2D with an N-terminally attached murine IgG1 Fc portion, to human NKG2D ligand on various tumor cell lines was assessed. Human NKG2D ligand was found to be present on Jurkat (T lymphocyte origin), RPMI8866 (B cell origin), K562 (erythroid origin), Daubi (B cell origin), and U937 (monocyte origin) tumor cell lines. Therefore, like the mouse chimeras, a human chimeric NKG2D construct can functionally recognize NKG2D ligand-bearing tumor cells.

The cytotoxic activity of human chimeric NKG2D-modified T cells against tumor cells was also determined. Human chimeric NKG2D-transduced primary human T cells were able to lyse mastocytoma cell line P815 transduced with human MIC-A (P815/MICA-A) in vitro (Table 6). The specificity of the interaction was apparent from the absence of lysis of wild-type P815 tumor cells and the absence of lysis by vector only-transduced T cells.

TABLE 6

| | Specific Lysis (%) Tumor Cell Line | | | | | |
|---|---|---|---|---|---|---|
| | P815/MIC-A | | | P815 | | |
| | Effector:Target Ratio | | | | | |
| | 1 | 5 | 25 | 1 | 5 | 25 |
| Vector Only | 0.0 | 0.0 | 0.6 | 0.0 | −0.6 | 0.0 |
| Human chimeric NKG2D | 5.4 | 17.3 | 35.4 | −2.5 | −0.3 | 1.1 |

Further, blocking of human chimeric NKG2D with an anti-NKG2D antibody prevented killing of K562 and RPMI8866 tumor cells by chimeric NKG2D-transduced human T cells (Table 7). These data demonstrate receptor specificity because a control antibody could not prevent killing.

TABLE 7

| | Specific Lysis (%) Tumor Cell Line | | | | | |
|---|---|---|---|---|---|---|
| | K562 | | | RPMI8866 | | |
| | Effector:Target Ratio | | | | | |
| | 1 | 5 | 25 | 1 | 5 | 25 |
| Vector + control antibody | 0.0 | 0.3 | 2.3 | 0.0 | 1.0 | 0.0 |
| Vector + anti-NKG2D antibody | 0.0 | 0.7 | 2.1 | 0.0 | 1.0 | 1.3 |
| Human chimeric NKG2D + control antibody | 3.1 | 17.6 | 53.8 | 9.3 | 27.4 | 41.6 |
| Human chimeric NKG2D + anti-NKG2D antibody | 1.6 | 10.1 | 27.0 | 1.0 | 2.5 | 7.5 |

Similar to the mouse studies, human chimeric NKG2D-transduced T cells produced high amounts of IFN-γ (~150-2250 pg/mL) after a 24 hour co-culture with tumor cells that express ligands for NKG2D (i.e., Jurkat, RPMI8866, K652, ECC-01 and P815/MIC-A tumor cells) compared with tumor cells that do not express NKG2D ligands (P815) or T cells incubated alone (Table 8). Vector only-transduced T cells did not produce IFN-γ, except against RPMI8866, indicating another ligand on this cell type for these activated T cells; however, IFN-γ production was almost 10-times as high with the human chimeric NKG2D-bearing T cells. Tumor cells alone produce no detectable IFN-γ.

TABLE 8

| | IFN-γ (Mean pg/mL ± SD) | | |
|---|---|---|---|
| Tumor cell Type | Chimeric NKG2D | Vector Only | Tumor cell control |
| P815 | 30.32 ± 1.31 | 15.11 ± 0.94 | 5.53 ± 1.31 |
| P815/MIC-A | 140.19 ± 5.91 | 9.19 ± 3.30 | 2.85 ± 1.50 |
| Jurkat | 182.66 ± 18.31 | 7.64 ± 1.04 | 2.83 ± 1.33 |
| RPMI8866 | 2239.95 ± 19.59 | 280.41 ± 13.84 | 2.47 ± 2.47 |
| K652 | 2305.46 ± 75.84 | 1.91 ± 0.57 | 1.82 ± 1.39 |
| ECC-1 | 469.97 ± 18.79 | 2.67 ± 2.67 | 0.00 ± 0.00 |
| T Cells only | 13.67 ± 2.55 | 0.94 ± 0.54 | N.D. |

Amounts represent the average of three experiments

Thus, having demonstrated the activation of host anti-tumor immunity and tumor elimination using chimeric NK cell receptors expressed in the T cells of an animal model of cancer and likewise demonstrated human tumor cell killing with human chimeric NK cell receptors, the present invention relates to a nucleic acid construct for expressing a chimeric receptor in host T cells to reduce or eliminate a tumor. The nucleic acid construct contains a first nucleic acid sequence encoding a promoter operably linked to a second nucleic acid sequence encoding a chimeric receptor protein containing a C-type lectin-like natural killer cell receptor, or a protein associated therewith, fused to an immune signaling receptor having an immunoreceptor tyrosine-based activation motif of SEQ ID NO:1. In general, the C-type lectin-like NK cell type II receptor (or a protein associated therewith) is located at the C-terminus of the chimeric receptor protein of the present invention whereas the immune signaling receptor is at the N-terminus, thereby facilitating intracellular signal transduction from the C-type lectin-like NK cell type II receptor.

A C-type lectin-like NK cell receptor protein particularly suitable for use in the chimeric receptor of the present invention includes a receptor expressed on the surface of natural killer cells, wherein upon binding to its cognate ligand(s) it alters NK cell activation. The receptor can work alone or in concert with other molecules. Ligands for these receptors are generally expressed on the surface of one or more tumor cell types, e.g., tumors associated with cancers of the colon, lung, breast, kidney, ovary, cervix, and prostate; melanomas; myelomas; leukemias; and lymphomas (Wu, et al. (2004) *J. Clin. Invest.* 114:60-568; Groh, et al. (1999) *Proc. Natl. Acad. Sci. USA* 96:6879-6884; Pende, et al. (2001) *Eur. J. Immunol.* 31:1076-1086) and are not widely expressed on the surface of cells of normal tissues. Examples of such ligands include, but are not limited to, MIC-A, MIC-B, heat shock proteins, ULBP binding proteins (e.g., ULPBs 1-4), and non-classical HLA molecules such as HLA-E and HLA-G, whereas classical MHC molecules such as HLA-A, HLA-B, or HLA-C and alleles thereof are not generally considered strong ligands of the C-type lectin-like NK cell receptor protein of the present invention. C-type lectin-like NK cell receptors which bind these ligands generally have a type II protein structure, wherein the N-terminal end of the protein is intracellular. Exemplary NK cell receptors of this type include, but are not limited to, Dectin-1 (GENBANK accession number AJ312373 or AJ312372), Mast cell function-associated antigen (GENBANK accession number AF097358), HNKR-P1A (GENBANK accession number U11276), LLT1 (GENBANK accession number AF133299), CD69 (GENBANK accession number NM_001781), CD69 homolog, CD72 (GENBANK accession number NM_001782), CD94 (GENBANK accession number NM_002262 or NM_007334), KLRF1 (GENBANK accession number NM_016523), Oxidised LDL receptor (GENBANK accession number NM_002543), CLEC-1, CLEC-2 (GENBANK accession number NM_016509), NKG2D (GENBANK accession number BC039836), NKG2C (GENBANK accession number AJ001684), NKG2A (GENBANK accession number AF461812), NKG2E (GENBANK accession number AF461157), WUGSC:H_DJ0701016.2, or Myeloid DAP12-associating lectin (MDL-1; GENBANK accession number AJ271684). In particular embodiments, the NK cell receptor is human NKG2D (SEQ ID NO:2) or human NKG2C (SEQ ID NO:3).

Similar type I receptors which would be useful in the chimeric receptor of the present invention include NKp46 (e.g., GENBANK accession number AJ001383), NKp30 (e.g., GENBANK accession number AB055881), or NKp44 (e.g., GENBANK accession number AJ225109).

As an alternative to the C-type lectin-like NK cell receptor protein, a protein associated with a C-type lectin-like NK cell receptor protein can be used in the chimeric receptor protein of the present invention. In general, proteins associated with C-type lectin-like NK cell receptor are defined as proteins that interact with the receptor and transduce signals therefrom. Suitable human proteins which function in this manner include, but are not limited to DAP10 (e.g., GENBANK accession number AF072845; SEQ ID NO:4) and DAP12 (e.g., GENBANK accession number AF019562; SEQ ID NO:5).

To the N-terminus of the C-type lectin-like NK cell receptor is fused an immune signaling receptor having an immunoreceptor tyrosine-based activation motif (ITAM), (Asp/Glu)-Xaa-Xaa-Tyr*-Xaa-Xaa-(Ile/Leu)-Xaa$_{6-8}$-Tyr*-Xaa-Xaa-(Ile/Leu) (SEQ ID NO:1) which is involved in the activation of cellular responses via immune receptors. Similarly, when employing a protein associated with a C-type lectin-like NK cell receptor, an immune signaling receptor can be fused to the C-terminus of said protein (FIG. 1). Suitable immune signaling receptors for use in the chimeric receptor of the present invention include, but are not limited to, the zeta chain of the T-cell receptor, the eta chain which differs from the zeta chain only in its most C-terminal exon as a result of alternative splicing of the zeta mRNA, the delta, gamma and epsilon chains of the T-cell receptor (CD3 chains) and the gamma subunit of the FcR1 receptor. In particular embodiments, the immune signaling receptor is CD3-zeta (CD3ζ) (e.g., GENBANK accession number human NM_198053; SEQ ID NO:6), or human Fc epsilon receptor-gamma chain (e.g., GENBANK accession number M33195; SEQ ID NO:7) or the cytoplasmic domain or a splicing variant thereof.

In particular embodiments, a chimeric receptor of the present invention is a fusion between NKG2D and CD3ζ or Dap10 and CD3ζ.

As used herein, a nucleic acid construct or nucleic acid sequence is intended to mean a DNA molecule which can be transformed or introduced into a T cell and be transcribed and translated to produce a product (e.g., a chimeric receptor or a suicide protein).

In the nucleic acid construct of the present invention, the promoter is operably linked to the nucleic acid sequence encoding the chimeric receptor of the present invention, i.e., they are positioned so as to promote transcription of the messenger RNA from the DNA encoding the chimeric receptor. The promoter can be of genomic origin or synthetically generated. A variety of promoters for use in T cells are well-known in the art (e.g., the CD4 promoter disclosed by Marodon, et al. (2003) *Blood* 101(9):3416-23). The promoter can be constitutive or inducible, where induction is associated with the specific cell type or a specific level of maturation. Alternatively, a number of well-known viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the chimeric receptor can be obtained from a genomic DNA source, a cDNA source, or can be synthesized (e.g., via PCR) or combinations thereof. Depending upon the size of the genomic DNA and the number of introns, it may be desirable to use cDNA or a combination thereof as it is found that introns stabilize the mRNA or provide T cell-specific expression (Barthel and Goldfeld (2003) *J. Immunol.* 171(7):3612-9). Also, it may be further advantageous to use endogenous or exogenous non-coding regions to stabilize the mRNA.

For expression of a chimeric receptor of the present invention, the naturally occurring or endogenous transcriptional initiation region of the nucleic acid sequence encoding N-terminal component of the chimeric receptor can be used to generate the chimeric receptor in the target host. Alternatively, an exogenous transcriptional initiation region can be used which allows for constitutive or inducible expression, wherein expression can be controlled depending upon the target host, the level of expression desired, the nature of the target host, and the like.

Likewise, the signal sequence directing the chimeric receptor to the surface membrane can be the endogenous signal sequence of N-terminal component of the chimeric receptor. Optionally, in some instances, it may be desirable to exchange this sequence for a different signal sequence. However, the signal sequence selected should be compatible with the secretory pathway of T cells so that the chimeric receptor is presented on the surface of the T cell.

Similarly, a termination region can be provided by the naturally occurring or endogenous transcriptional termination region of the nucleic acid sequence encoding the C-terminal component of the chimeric receptor. Alternatively, the termination region can be derived from a different source. For the most part, the source of the termination region is generally not considered to be critical to the expression of a recombinant protein and a wide variety of termination regions can be employed without adversely affecting expression.

As will be appreciated by one of skill in the art, in some instances, a few amino acids at the ends of the C-type lectin-like natural killer cell receptor (or protein associated therewith) or immune signaling receptor can be deleted, usually not more than 10, more usually not more than 5 residues. Also, it may be desirable to introduce a small number of amino acids at the borders, usually not more than 10, more usually not more than 5 residues. The deletion or insertion of amino acids will usually be as a result of the needs of the construction, providing for convenient restriction sites, ease of manipulation, improvement in levels of expression, or the like. In addition, the substitute of one or more amino acids with a different amino acid can occur for similar reasons, usually not substituting more than about five amino acids in any one domain.

The chimeric construct, which encodes the chimeric receptor according to this invention can be prepared in conventional ways. Since, for the most part, natural sequences are employed, the natural genes are isolated and manipulated, as appropriate (e.g., when employing a Type II receptor, the immune signaling receptor component may have to be inverted), so as to allow for the proper joining of the various components. Thus, the nucleic acid sequences encoding for the N-terminal and C-terminal proteins of the chimeric receptor can be isolated by employing the polymerase chain reaction (PCR), using appropriate primers which result in deletion of the undesired portions of the gene. Alternatively, restriction digests of cloned genes can be used to generate the chimeric construct. In either case, the sequences can be selected to provide for restriction sites which are blunt-ended, or have complementary overlaps.

The various manipulations for preparing the chimeric construct can be carried out in vitro and in particular embodiments the chimeric construct is introduced into vectors for cloning and expression in an appropriate host using standard transformation or transfection methods. Thus, after each manipulation, the resulting construct from joining of the DNA sequences is cloned, the vector isolated, and the sequence screened to insure that the sequence encodes the desired chimeric receptor. The sequence can be screened by restriction analysis, sequencing, or the like.

The chimeric constructs of the present invention find application in subjects having or suspected of having cancer by reducing the size of a tumor or preventing the growth or regrowth of a tumor in these subjects. Accordingly, the present invention further relates to a method for reducing growth or preventing tumor formation in a subject by introducing a chimeric construct of the present invention into an isolated T cell of the subject and reintroducing into the subject the transformed T cell thereby effecting anti-tumor responses to reduce or eliminate tumors in the subject. Suitable T cells which can be used include, cytotoxic lymphocytes (CTL), tumor-infiltrating-lymphocytes (TIL) or other cells which are capable of killing target cells when activated. As is well-known to one of skill in the art, various methods are readily available for isolating these cells from a subject. For example, using cell surface marker expression or using commercially available kits (e.g., ISOCELL™ from Pierce, Rockford, Ill.).

While the present invention relates to the elimination of tumors, the chimeric NK receptors of the present invention may also be useful for treatment of other diseases where these ligands may be present. For example, the immune response can be down-modulated during autoimmune disease or transplantation by expressing these type of chimeric NK receptors in T regulatory or T suppressor cells. Thus, these cells would mediate their regulatory/suppressive function only in the location where the body has upregulated one of the ligands for these receptors. This ligand upregulation may occur during stress or inflammatory responses.

It is contemplated that the chimeric construct can be introduced into the subject's own T cells as naked DNA or in a suitable vector. Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention.

Alternatively, a viral vector (e.g., a retroviral vector, adenoviral vector, adeno-associated viral vector, or lentiviral vector) can be used to introduce the chimeric construct into T cells. Suitable vectors for use in accordance with the method of the present invention are non-replicating in the subject's T cells. A large number of vectors are known which are based on viruses, where the copy number of the virus maintained in the cell is low enough to maintain the viability of the cell. Illustrative vectors include the pFB-neo vectors (STRATAGENE®) disclosed herein as well as vectors based on HIV, SV40, EBV, HSV or BPV.

Once it is established that the transfected or transduced T cell is capable of expressing the chimeric receptor as a surface membrane protein with the desired regulation and at a desired level, it can be determined whether the chimeric receptor is functional in the host cell to provide for the desired signal induction (e.g., production of Rantes, Mip1-alpha, GM-CSF upon stimulation with the appropriate ligand).

Subsequently, the transduced T cells are reintroduced or administered to the subject to activate anti-tumor responses in said subject. To facilitate administration, the transduced T cells according to the invention can be made into a pharmaceutical composition or made implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed which does not ineffectuate the cells expressing the chimeric receptor. Thus, desirably the transduced T cells can be made into a pharmaceutical composition containing a balanced salt solution, preferably Hanks' balanced salt solution, or normal saline.

A pharmaceutical composition of the present invention can be used alone or in combination with other well-established agents useful for treating cancer. Whether delivered alone or in combination with other agents, the pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

A composition of the present invention can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular subject.

Desirably an effective amount or sufficient number of the isolated transduced T cells is present in the composition and introduced into the subject such that long-term, specific, anti-tumor responses are established to reduce the size of a tumor or eliminate tumor growth or regrowth than would otherwise result in the absence of such treatment. Desirably, the amount of transduced T cells reintroduced into the subject causes a 10%, 20%, 30%, 40%, 50%, 60%, 70%, 80%, 90%, 95%, 98%, or 100% decrease in tumor size when compared to otherwise same conditions wherein the transduced T cells are not present.

Accordingly, the amount of transduced T cells administered should take into account the route of administration and should be such that a sufficient number of the transduced T cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1\times10^6$ to about $1\times10^9$ transduced T cells, even more desirably, from about $1\times10^7$ to about $5\times10^8$ transduced T cells, although any suitable amount can be utilized either above, e.g., greater than $5\times10^8$ cells, or below, e.g., less than $1\times10^7$ cells. The dosing schedule can be based on well-established cell-based therapies (see, e.g., Topalian and Rosenberg (1987) *Acta Haematol.* 78 Suppl 1:75-6; U.S. Pat. No. 4,690, 915) or an alternate continuous infusion strategy can be employed.

These values provide general guidance of the range of transduced T cells to be utilized by the practitioner upon optimizing the method of the present invention for practice of the invention. The recitation herein of such ranges by no means precludes the use of a higher or lower amount of a component, as might be warranted in a particular application.

For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

In particular embodiments, the chimeric nucleic acid construct further contains a suicide gene such as thymidine kinase (TK) of the HSV virus (herpesvirus) type I (Bonini, et al. (1997) *Science* 276:1719-1724), a Fas-based "artificial suicide gene" (Thomis, et al. (2001) *Blood* 97:1249-1257), or *E. coli* cytosine deaminase gene which are activated by gancyclovir, AP1903, or 5-fluorocytosine, respectively. The suicide gene is advantageously included in the nucleic acid construct of the present invention to provide for the opportunity to ablate the transduced T cells in case of toxicity and to destroy the chimeric construct once a tumor has been reduced or eliminated. The use of suicide genes for eliminating transformed or transduced cells is well-known in the art. For example, Bonini, et al. ((1997) *Science* 276:1719-1724) teach that donor lymphocytes transduced with the HSV-TK suicide gene provide antitumor activity in patients for up to one year and elimination of the transduced cells is achieved using ganciclovir. Further, Gonzalez, et al. ((2004) *J. Gene Med.* 6:704-711) describe the targeting of neuroblastoma with cytotoxic T lymphocyte clones genetically modified to express a chimeric scFvFc: ζ immunoreceptor specific for an epitope on L1-CAM, wherein the construct further expresses the hygromycin thymidine kinase (HyTK) suicide gene to eliminate the transgenic clones.

It is contemplated that the suicide gene can be expressed from the same promoter as the chimeric receptor or from a different promoter. Generally, however, nucleic acid sequences encoding the suicide protein and chimeric receptor reside on the same construct or vector. Expression of the suicide gene from the same promoter as the chimeric receptor can be accomplished using any well-known internal ribosome entry site (IRES). Suitable IRES sequences which can be used in the nucleic acid construct of the present invention include, but are not limited to, IRES from EMCV, c-myc, FGF-2, poliovirus and HTLV-1. By way of illustration, a nucleic acid construct for expressing a chimeric receptor can have the following structure: promoter→chimeric receptor→IRES→suicidal gene. Alternatively, the suicide gene can be expressed from a different promoter than that of the chimeric receptor (e.g., promoter 1→chimeric receptor→promoter 2→suicidal gene).

The following non-limiting examples are presented to better illustrate the invention.

Example 1

Mice and Cell Lines

C57BL/6 mice were purchased from the National Cancer Institute, and all animal work was conducted in accordance with standard guidelines.

Cell lines Bosc23, PT67, GP+E86, EG7 (H-2$^b$), and YAC-1 were obtained from the American Type Culture Collection (ATCC, Rockville, Md.). RMA cells (H-2$^b$) originated from a Rauscher virus-induced C57BL/6 T-cell lymphoma (Ljunggren and Karre (1985) *J. Exp. Med.* 162:1745-1759). RMA-S is a sub-line of RMA which lacks MHC class-I surface expression (Kärre, et al. (1986) *Nature* 319:675-678). All packaging cells were grown in Dulbecco's modified Eagle medium (DMEM) with a high glucose concentration (4.5 gram/liter) supplemented with 10% heat-inactivated fetal bovine serum (FBS; Hyclone, Logan, Utah), 20 U/mL penicillin, 20 µg/mL streptomycin, 1 mM pyruvate, 10 mM HEPES, 0.1 mM non-essential amino acids, 50 µM 2-mercaptoethanol. RMA, EG7, RMA-S and YAC-1 cells were cultured in RPMI plus the same supplements described above.

Example 2

Retroviral Vector Construction

The full-length murine NKG2D cDNA was purchased from Open Biosystems (Huntsville, Ala.). Murine CD3ζ chain, Dap10 and Dap12 cDNAs were cloned by RT-PCR using RNAs from ConA- or IL-2 (1000 U/mL)-activated spleen cells as templates. Mouse NKG2D ligands Rae-1β and H60 were cloned from YAC-1 cells by RT-PCR. All PCR reactions were performed using high-fidelity enzyme Pfu or PFUULTRA™ (STRATAGENE®, La Jolla, Calif.). The oligonucleotides employed in these PCR reactions are listed in Table 9.

TABLE 9

| No. | Primer | | Sequence | SEQ ID NO: |
|---|---|---|---|---|
| 1 | 5' | wtNKG2D | GCG<u>GAATTC</u>GCCACCATGGCATTGATTCGTGATCGA | 8 |
| 2 | 3' | wtNKG2D | GGCG<u>CTCGAG</u>TTACACCGCCCTTTTCATGCAGAT | 9 |
| 3 | 5' | chNKG2D | GGC<u>GAATT</u>CGCATTGATTCGTGATCGAAAGTCT | 10 |
| 4 | 5' | wtDAP10 | GCAA<u>GTCGAC</u>GCCACCATGGACCCCCCAGGCTACC | 11 |
| 5 | 3' | wtDAP10 | GGC<u>GAATTC</u>TCAGCCTCTGCCAGGCATGTTGAT | 12 |
| 6 | 3' | chDAP10 | GGCA<u>GAATTC</u>GCCTCTGCCAGGCATGTTGATGTA | 13 |
| 7 | 5' | wtDAP12 | GTTA<u>GAATTC</u>GCCACCATGGGGGCTCTGGAGCCCT | 14 |
| 8 | 3' | wtDAP12 | GCAA<u>CTCGAG</u>TCATCTGTAATATTGCCTCTGTG | 15 |
| 9 | 5' | ATG-CD3ζ | GGC<u>GTCGAC</u>ACCATGAGAGCAAAATTCAGCAGGAG | 16 |
| 10 | 3' | ATG-CD3ζ | GCTT<u>GAATTC</u>GCGAGGGGCCAGGGTCTGCATAT | 17 |
| 11 | 5' | CD3ζ-TAA | GCA<u>GAATTC</u>AGAGCAAAATTCAGCAGGAGTGC | 18 |
| 12 | 3' | CD3ζ-TAA | GCTTT<u>CTCGAG</u>TTAGCGAGGGGCCAGGGTCTGCAT | 19 |
| 13 | 5' | Rae-1 | GCAT<u>GTCGAC</u>GCCACCATGGCCAAGGCAGCAGTGA | 20 |
| 14 | 3' | Rae-1 | GCGG<u>CTCGAG</u>TCACATCGCAAATGCAAATGC | 21 |
| 15 | 5' | H60 | GTTA<u>GAATTC</u>GCCACCATGGCAAAGGGAGCCACC | 22 |
| 16 | 3' | H60 | GCG<u>CTCGAG</u>TCATTTTTTCTTCAGCATACACCAAG | 23 |

Restriction sites inserted for cloning purposes are underlined.

Chimeric NKG2D was created by fusing the murine CD3ζ chain cytoplasmic region coding sequence (CD3ζ-CYP) to the full-length gene of murine NKG2D. Briefly, the SalI-EcoRI fragment of CD3ζ-CYP (with the initiation codon ATG at the 5' end, primer numbers 9 and 10) and the EcoRI-XhoI fragment of NKG2D (without ATG, primer numbers 2 and 3) were ligated into the SalI/XhoI-digested pFB-neo retroviral vector (STRATAGENE®, La Jolla, Calif.). Similarly, chimeric Dap10 was generated by fusing the SalI-EcoRI fragment of full-length Dap10 (primer numbers 4 and 6) to the EcoRI-XhoI fragment of CD3ζ-CYP (primer numbers 11 and 12). Wild-type NKG2D (primer numbers 2 and 3), Dap10 (primer numbers 4 and 5) and Dap12 (primer numbers 7 and 8) fragments were inserted between the EcoRI and XhoI sites in pFB-neo. In some cases, a modified vector pFB-IRES-GFP was used to allow co-expression of green fluorescent protein (GFP) with genes of interest. pFB-IRES-GFP was constructed by replacing the 3.9 kb AvrI/ScaI fragment of pFB-neo with the 3.6 kb AvrII/ScaI fragment of a plasmid GFP-RV (Ouyang, et al. (1998) *Immunity* 9:745-755). Rae-1β (primer numbers 13 and 14) and H60 (primer numbers 15 and 16) cDNAs were cloned into pFB-neo. Constructs containing human NKD2D and human CD3ζ (or murine Fc were prepared in the same manner using the appropriate cDNAs as templates.

Example 3

Retrovirus Production and Transduction

Eighteen hours before transfection, Bosc23 cells were plated in 25 cm² flasks at a density of 4×10⁶ cells per flask in 6 mL of DMEM-10. Transfection of retroviral constructs into Bosc23 cells was performed using LIPOFECTAMINE™ 2000 (INVITROGEN™, Carlsbad, Calif.) according to the manufacturer's instruction. Viral supernatants were collected 48 and 72 hours post-transfection and filtered (0.45 μm) before use. For generation of large scale, high-titer ecotropic vectors, the ecotropic viruses produced above were used to transduce the dualtropic packaging cell PT67 in the presence of polybrene (8 μg/mL). After three rounds of transduction, PT67 cells were selected in G418 (1 mg/mL) for 7 days. Dualtropic vectors were then used to transduce ecotropic cell line GP+E86. Through this process, the virus titer from pooled GP+E86 cells generally was over 1×10⁶ CFU/mL. Concentration of retroviruses by polyethylene glycol (PEG) was performed according to standard methods (Zhang, et al. (2004) *Cancer Gene Ther.* 11:487-496; Zhang, et al. (2003) *J. Hametother. Stem Cell Res.* 12:123-130). Viral stocks with high titer (1~2×10⁷ CFU/mL) were used for transduction of T cells. Primary T cells from spleens of C57BL/6 (B6) mice were infected 18-24 hours after concanavalin A (ConA, 1 μg/mL) stimulation based on a well-established protocol (Sentman, et al. (1994) *J. Immunol.* 153:5482-5490). Two days after infection, transduced primary T cells (0.5~1×10⁶/mL) were selected in RPMI-10 media containing G418 (0.5 mg/mL) plus 25 U/mL rHuIL-2 for an additional 3 days. Viable cells were isolated using HISTOPAQUE®-1083 (Sigma, St. Louise, Mo.) and expanded for 2 days without G418 before functional analyses. NKG2D ligand-expressing RMA (RMA/Rae-1β and RMA/H60) or RMA-S (RMA-S/Rae-1β) cells were established by retroviral transduction with dualtropic vectors from PT67.

Example 4

Cytokine Production by Gene-Modified T Cells

Gene-modified primary T cells (10⁵) were co-cultured with an equal number of RMA, RMA/Rae-1β, RMA/H60 or YAC-1 cells in 96-well plates in complete media. After twenty-four hours, cell-free supernatants were collected. IFN-γ was assayed by ELISA using a DUOSET® ELISA kits (R&D, Minneapolis, Minn.). In some cases, T cells were cultured with equal numbers of irradiated (100 Gys) tumor cells for 3 days. Detection of other cytokines in culture was performed using a BIO-PLEX® kit (BIO-RAD®, Hercules, Calif.) based on the manufacturer's protocol.

Example 5

Flow Cytometry

For FACS analysis of NKG2D ligand expression, tumor cells were stained with mouse NKG2D-Ig fusion protein (R&D systems) according to manufacturer's instruction. Cell-surface phenotyping of transduced primary T cells was determined by direct staining with APC-anti-CD3ε (clone 145-2C11; Pharmingen, San Diego, Calif.), PE-anti-NKG2D (clone 16-10A1; eBioscience, San Diego, Calif.) and FITC-anti-CD4 (Clone RM4-5; Caltag, Burlingame, Calif.) monoclonal antibodies. Cell fluorescence was monitored using a FACSCALIBER™ cytometer. Sorting of NKG2D ligand-expressing cells was performed on a FACSTARM™ cell sorter (Becton Dickinson, San Jose, Calif.).

Example 6

Cytotoxicity Assay

Three or four days after G418 selection (0.5 mg/mL), retroviral vector-transduced primary T cells were cultured in complete RPMI media containing 25 U/mL human IL-2 for an additional 2-3 days. Viable lymphocytes were recovered by centrifugation over HISTOPAQUE®-1083 (Sigma, St. Louis, Mo.) and used as effector cells. Lysis of target cells (RMA, RMA/Rae-1β, RMA/H60, EG7, RMA-S, RMA-S/Rae-1β, and YAC-1) was determined by a 4-hour $^{51}$Cr release assay (Sentman, et al. (1994) supra). To block NKG2D receptors, anti-NKG2D (clone: CX5, 20 μg/mL) was included in those assays. The percentage of specific lysis was calculated as follows: % Specific lysis=[(Specific $^{51}$Cr release−spontaneous $^{51}$Cr release)/(Maximal $^{51}$Cr release−spontaneous $^{51}$Cr release)]×100.

Example 7

Treatment of Mice with Genetically Modified T Cells

For the determination of direct effects of chimeric NKG2D-bearing T cells (10⁶) on the growth of RMA or RMA/Rae-1β tumors, chimeric NKG2D- or vector-transduced T cells were mixed with tumor cells (10⁵) and then injected s.c. into the shaved right flank of recipient mice. Tumors were then measured using a caliper, and tumor areas were calculated. Animals were regarded as tumor-free when no tumor was found four weeks after inoculation. For the rechallenge experiments, mice were inoculated with $10^4$ RMA cells on the shaved left flank. In other experiments, transduced T cells were injected intravenously the day before s.c. inoculation of tumor cells. Mice were monitored for tumor size every two days and were sacrificed when tumor burden became excessive.

Example 8

Statistical Analysis

Differences between groups were analyzed using the student's t-test. p values <0.05 were considered significant.

---

What is claimed is:

1. A nucleic acid construct for expressing a chimeric receptor comprising:
a first nucleic acid sequence encoding a promoter operably linked to a second nucleic acid sequence encoding a chimeric receptor comprising a C-type lectin-like natural killer cell receptor, fused to a nucleic acid encoding an immune signaling receptor containing an immunoreceptor tyrosine-based activation motif of SEQ ID NO: 1.

2. The nucleic acid construct of claim 1, wherein the construct is in a vector.

3. The nucleic acid construct of claim 1 further comprising a suicide gene.

4. An isolated T cell comprising the nucleic acid construct of claim 1 or 3, or the vector of claim 2.

* * * * *

SEQUENCE LISTING

<160> NUMBER OF SEQ ID NOS: 23

<210> SEQ ID NO 1
<211> LENGTH: 19
<212> TYPE: PRT
<213> ORGANISM: Artificial Sequence
<220> FEATURE:
<223> OTHER INFORMATION: Consensus immunoreceptor tyrosine-based
      activation motif
<220> FEATURE:
<221> NAME/KEY: MISC_FEATURE
<222> LOCATION: (1)..(1)
<223> OTHER INFORMATION: Xaa denotes Asp or Glu
<220> FEATURE:
<221> NAME/KEY: MISC_FEATURE
<222> LOCATION: (2)..(3)
<223> OTHER INFORMATION: Xaa denotes any amino acid residue
<220> FEATURE:
<221> NAME/KEY: MISC_FEATURE
<222> LOCATION: (5)..(6)
<223> OTHER INFORMATION: Xaa denotes any amino acid residue
<220> FEATURE:
<221> NAME/KEY: MISC_FEATURE
<222> LOCATION: (7)..(7)
<223> OTHER INFORMATION: Xaa denotes Ile or Leu
<220> FEATURE:
<221> NAME/KEY: MISC_FEATURE
<222> LOCATION: (8)..(13)
<223> OTHER INFORMATION: Xaa denotes any amino acid residue
<220> FEATURE:
<221> NAME/KEY: MISC_FEATURE
<222> LOCATION: (14)..(14)
<223> OTHER INFORMATION: Xaa is absent or denotes any amino acid residue
<220> FEATURE:
<221> NAME/KEY: MISC_FEATURE
<222> LOCATION: (15)..(15)
<223> OTHER INFORMATION: Xaa is absent or denotes any amino acid residue
<220> FEATURE:
<221> NAME/KEY: MISC_FEATURE
<222> LOCATION: (17)..(18)
<223> OTHER INFORMATION: Xaa denotes any amino acid residue
<220> FEATURE:
<221> NAME/KEY: MISC_FEATURE
<222> LOCATION: (19)..(19)
<223> OTHER INFORMATION: Xaa denotes Ile or Leu

<400> SEQUENCE: 1

Xaa Xaa Xaa Tyr Xaa Xaa Xaa Xaa Xaa Xaa Xaa Xaa Xaa Xaa Xaa Tyr
1               5                   10                  15

Xaa Xaa Xaa

<210> SEQ ID NO 2
<211> LENGTH: 1575
<212> TYPE: DNA
<213> ORGANISM: Homo sapiens

<400> SEQUENCE: 2
tgaggacata tctaaatttt ctagttttat agaaggcttt tatccacaag aatcaagatc      60

```
ttccctctct gagcaggaat cctttgtgca ttgaagactt tagattcctc tctgcggtag      120
acgtgcactt ataagtattt gatggggtgg attcgtggtc ggaggtctcg acacagctgg      180
gagatgagtg aatttcataa ttataacttg gatctgaaga agagtgattt ttcaacacga      240
tggcaaaagc aaagatgtcc agtagtcaaa agcaaatgta gagaaaatgc atctccattt      300
tttttctgct gcttcatcgc tgtagccatg ggaatccgtt tcattattat ggtagcaata      360
tggagtgctg tattcctaaa ctcattattc aaccaagaag ttcaaattcc cttgaccgaa      420
agttactgtg gcccatgtcc taaaaactgg atatgttaca aaaataactg ctaccaattt      480
tttgatgaga gtaaaaactg gtatgagagc caggcttctt gtatgtctca aaatgccagc      540
cttctgaaag tatacagcaa agaggaccag gatttactta aactggtgaa gtcatatcat      600
tggatgggac tagtacacat tccaacaaat ggatcttggc agtgggaaga tggctccatt      660
ctctcaccca acctactaac aataattgaa atgcagaagg gagactgtgc actctatgcc      720
tcgagcttta aaggctatat agaaaactgt tcaactccaa atacatacat ctgcatgcaa      780
aggactgtgt aaagatgatc aaccatctca ataaagcca ggaacagaga agagattaca      840
ccagcggtaa cactgccaac cgagactaaa ggaaacaaac aaaaacagga caaaatgacc      900
aaagactgtc agatttctta gactccacag gaccaaacca tagaacaatt tcactgcaaa      960
catgcatgat tctccaagac aaaagaagag agatcctaaa ggcaattcag atatccccaa     1020
ggctgcctct cccaccacag gcccagagtg gatgggctgg gggaggggtg ctgtttttaat    1080 ttctaaaggt aggaccaaca cccaggggat cagtgaagga agagaaggcc agcagatcag     1140
tgagagtgca accccaccct ccacaggaaa ttgcctcatg gcagggcca cagcagagag       1200 acacagcatg ggcagtgcct tccctgcctg tgggggtcat gctgccactt ttaatgggtc     1260
ctccacccaa cggggtcagg gaggtggtgc tgccctagtg ggccatgatt atcttaaagg     1320
cattattctc cagccttaag atcttaggac gtttcctttg ctatgatttg tacttgcttg     1380
agtcccatga ctgtttctct tcctctcttt cttccttttg gaatagtaat atccatccta     1440
tgtttgtccc actattgtat tttgaaagca cataacttgt ttggtttcac aggttcacag     1500
ttaagaagga attttgcctc tgaataaata gaatcttgag tctcatgcaa aaaaaaaaa      1560 aaaaaaaaaa aaaaa                                                      1575
```

<210> SEQ ID NO 3
<211> LENGTH: 6098
<212> TYPE: DNA
<213> ORGANISM: Homo sapiens

<400> SEQUENCE: 3

```
gcagttatca tagagcacag tccctcacat cacacagctg cagagatgag taaacaaaga      60
ggaaccttct cagaagtgag tctggcccag gaccccaaagc ggcagcaaag gaaacctaaa    120
ggcaataaaa gctccatttc aggaaccgaa caggaaatat tccaagtaga attaaatctt     180
caaaatcctt ccctgaatca tcaagggatt gataaaatat atgactgcca aggtaaaaca     240
ttaaatatat cttcaatatt attgttctag gatgtgcagt tgaatgcaga agggtgagga     300
aagattaggg aatattttgc acttgtgaga atcggagttc ataattggga tctaaaattc     360
taatatgaaa tcagaagact aattttattc gggcattgtt caactgtaat ctgcggtcca     420
ctcatggaac attatatttta ctgaaaatga aatggtatat tctgagagaa agattactag    480
agtagatgta gatttagagg ccagagttta tcattatgtt tccctgtgca tgtgggttct     540
ctagtatgta attctctagt atgtaatcct aatcaactct ctatctcccc tctctcagtg     600
```

```
cctctatttc tctccctgca ggtttactgc cacctccaga gaagctcact gccgaggtcc    660
taggaatcat ttgcattgtc ctgatggcca ctgtgttaaa acaatagtt cttattcctt     720 gtaagcatat tcttgaaaga ttagaaggga acgttttact ttaatgcttg gaagtgcctc    780
aaaatatttc atactgttga agaatagaac tcttatttta ctgtttcttt caagatcta     840 ttacttcatt tatttttata gaaaagtta attttattaa agattgtccc cattttaaat    900
aacacacaaa gtttcaaagt aagaaactaa actcattatg gtttatctaa atattactttt    960 ttataaaaat catttaatt tttctgttac agtcctggaa cagaacaatt cttccccaaa    1020
tacaagaacc cagaaaagta cattttatt ttcaaagttc tgatattagt acaatttgga   1080
accaaaagta atatggttat tctgaatttt tcacaacata ataacaaaa tcattgtaga    1140 gaacatgtgt ttattttttg tgtgtaatct atatatatgt atatacatac acacacaaag   1200
atattttctg atttcataat tcaaaggcat gctatagaag aaaagtattt agaaaaacaa   1260
attaattttt gaaagtggtt acatcaaata ctacaagaga tggtgaagtt tgtgctaaag   1320 tcttaaaaa tgtttatttc aaaggtctat tacttttat attttttatag aaaaagttaa   1380 ttttattaaa gattctcccc attttaaata acacacaaag tttcaaagta agaaactaaa   1440
ctcgttatgg ttcatctaga tatcagtttt tataaaaatc attttaattt ttctattaca   1500
gtcctggagc agaacaattc ttccccgaat acaagaacgc agaaaggtac atttttattt   1560
tcaatgttct gatattagta caattatat tttgtgtctg ttttaaggca tgtaaaagaa    1620
tagtggcatt tttgcagaaa ataagccata aattcagcca taaatatttg taagaaaga    1680 ttatgaggca gcatttcctt ttctccagtg agtagaaata ctcacttaaa atcattctac   1740
cctctttctc ccaattaaca gaggtttcct actgctgtga gatgatacca aataaataat   1800
tttactattc taaaaaagca gttgtgtatc agcgatgttc aacacatgtg tagagtgtat   1860
ttttgtttgt tcatttgctt tatatgggaa cacaattagg gaggagaggc taacccttgt   1920
ctgtgcatgt gtgtatgact gactcagtta ttaaaaatat acatttataa gcctgtaagg   1980
atgcgtaaat atgttaagca catatatgtt tatactgttg aaatatgtga actaattttc   2040
atttttaaaa attcatattg gtctaaatag taattcatat ctttattagc acgtcattgt   2100
ggccattgtc ctgaggagtg gattacatat tccaacagtt gttattacat tggtaaggaa    2160
agaagaactt gggaagagag tttgctggcc tgtacttcga agaactccag tctgctttct    2220
atagataatg aagaagaaat ggtaagatgt aaatgtttca aacattttat gaaaagcttc    2280
cttcagtgaa taatacattt gtagaaaaca tccatatgtg tgtacatata tttatctcat    2340
atattttcaa gtgtatgtaa tattcaattg attgacttaa taatgttttt aaagttatat    2400
actgctaatg tacatttatt ttcagttttt gttttttcaag gaaaaccatg cttctataag    2460
tgctttgaat ccacaataaa ttttgctatc taattttatc gggcatgata tcatctggtc    2520
atgcagattg atcacaaagt gaatgaatgc atgtgataca agtcagatca tgaaataaaa    2580
gtttccagct ctagcagttc caccctgtg tatgccctca tcacttatcc tgactcctct    2640
ccaaaacgca gtcttgactt taatattat aaataatgat tgcctgttct tgaattttatt   2700 tatataaagg gaatcaaaca gtgtgaattt catgtctttt tcaatcctat ctgatatttg    2760
tgcaattcct ccatattatt gcagttatca gtagtatgtt actgttcact gctgtactat    2820
gtacaaagaa cagtaagaat ccattgagtc cttgtctctg gatggggaag tgggtctcat    2880
gccctcaggg acaaagagga ccctaggtgg tttacggtgc actgttagtc atggggtccc    2940
tttgctgatc ctcctcatcc acagccatcc tggtgtctct tggtatgaga aggaagcact    3000
```

```
ttctctagct ccatattggt agcaggtctc ctggtagatc atccttgcca gtggcaccag   3060
ccttgcctgg tattgtggag gggactctcc ttcgataccc tcctcctatt gccaggttgg   3120
gtgtagggaa acagcaggcc taggtcacct tcttctgtcg tgtggaggac ttaacatgct   3180
cacttggaca cttggttgat ccctgatgct agggtcccag acaatttcat ctttctcttt   3240
ccacctttca gagttctcca ttgcttttgt ctttcattaa tcccagagtt tatagttgtt   3300
tttagtaggg agtagcagag agagacgagt ctacaccacc tggccaggac ccctgttatt   3360
ccgcaaaaac cgaatcggat aaaaattgag ggcttatcta gttaaagaat ggtgtggtac   3420
ccagaaaacc caatctgtag cttccatgtc atctatttct gaatgacaac ccctcaattc   3480
ccttctaaat ctccaactct gagaaatata gcacaaaaat agattgattt agtcacagta   3540
tctggagaaa tgaatgcaca gtatcaggaa acttattaaa acccttcctg tgtttattct   3600
gttaattgga gtaactatta cattgcaaga attaaaatgt ctttattaac atgagaataa   3660
gaatgaaagt actaagtata aacgttgaag agttcattta aataaaaaat tcaaacattt   3720
atgaaagttt ttggcactgc aaatagtggt tttcaacttt aatatattgt ttttgtaatg   3780
ttttcataat tattatttaa gtgaaaatta tttcttttct tttagaaatt tctggccagc   3840
attttacctt cctcatggat tggtgtgttt cgtaacagca gtcatcatcc atgggtgaca   3900
ataaatggtt tggcttttcaa acataagtaa gttcttttgt atggcgctat ataaaaaata   3960
tatataaagg ataaattcag aagaataata tgaataaatt tatgtggaat cattgacatg   4020
aagaaagatg tggaaagtta gtgaaatgtt gatataaata ttttacaata gaccatagta   4080
gtccatatat ttcaaccgct cattggtctg ctagtaacct tcttggttat cagatggacc   4140
aggggtgtcc catctttggc ttctgtgggc cacgttagaa gacgaatagt cttggcccac   4200
acatagaata cactaacact aacgatagct gacgagctaa aaaaaaaaa aaatcacaga   4260 atgttttaag aaagtttacg tatttgtgtt gggccgcatt caaagctgtc ctgggtcacg   4320
tgcggcccat gggcagcgag ttggacaacc tcgagctgga ctatcaggga actgcagtgc   4380
ttgtttttat taaaaagcca cgcttacttt tttacttaag aatatcctca agcacaata   4440 atagtgctgt tggcatattg ctataatttt tttattacta gttattgttg tcaatctctt   4500
attgtgccta atttataaat taaactttat cacagttatg aatgtgtaga gaaaacataa   4560
tctctctata ggttctgcac tatctgccat ttcaggcatc cactggggtc ttgaaacata   4620
tccctcgtgg atgaagaggg actactctgt tgagtgttca gaataatgac tcttactaat   4680
attatgaaaa atttaattac cctttttccat gaaattcttt tcttacagta catggaaaat   4740
gctttcgtct catgaatcat ttgcttaaaa tgtaacagaa tatggatttt tctccattac   4800
aggataaaag actcagataa tgctgaactt aactgtgcag tgctacaagt aaatcgactt   4860
aaatcagccc agtgtggatc ttcaatgata tatcattgta agcataagct ttagaagtaa   4920
agcatttgcg tttacagtgc atcagataca ttttatattt cttaaaatag aaatattatg   4980
attgcataaa tctgaaaatg aattatgtta tttgctctaa tacaaaaatt ctaaatcaat   5040
tattgaaata ggatgcacac aattactaaa gtacagacat cctagcattt gtgtcgggct   5100
cattttgctc aacatggtat ttgtggtttt cagcctttct aaaagttgca tgttatgtga   5160
gtcagcttat aggaagtacc aagaacagtc aaacccatgg agacagaaag tagaatagtg   5220
gttgccaatg tctcagggag gttgaaatag gagatgacca ctaattgata gaacgtttct   5280
ttgtgtcgtg atgaaaactt tctaaatttc agtaatggtg atggttgtaa ctttgcgaat   5340
atactaaaca tcattgatttt ttaatcattt taagtgcatg aaatgtatgc tttgtacatg   5400
```

| | |
|---|---|
| acacttcaat aaagctatcc agaaaaaaaa aagcctctga tgggattgtt tatgactgca | 5460 |
| tttatctcta aagtaatttt aaagattagc ttctttataa tattgacttt tctaatcagt | 5520 |
| ataaagtgtt tccttcaatg tactgtgtta tctttaattt ctctctcttg tattttgtat | 5580 |
| tttgggggat tgaagtcata cagaaatgta ggtattttac atttatgctt ttgtaaatgg | 5640 |
| catcctgatt ctaaaattcc ctttagtaat ttttgttgtt ataaatagaa atacaactga | 5700 |
| tgtctgcatt ttgattttat atctacttat tccactgatt ttatatattt aaatctatta | 5760 |
| tgtcaactat tgatttattt ctgggtgttc tatataacga gcaattttat ctgcaaatga | 5820 |
| tcacactttt attttttta atccatgtgc tataacttag ttttattttc atttattttc | 5880 |
| actggctaag gttttatacc catagttgaa tagaaggcac aatcaaagtt ctttgtggat | 5940 |
| catatgcatc attttctggt tttggcaaaa aatacttcaa catgttatac atatttaaaa | 6000 |
| agcttggtgt tttttgcatc ctatctttct catatcgaag cagttttata atcctatttt | 6060 |
| ctaatagatt ttatcaattg taacaatttt tattaatt | 6098 |

<210> SEQ ID NO 4
<211> LENGTH: 3000
<212> TYPE: DNA
<213> ORGANISM: Homo sapiens

<400> SEQUENCE: 4

| | |
|---|---|
| aattcccagc cctggagctg gcattccagt gggaggccac tctcagtttc acttggtgac | 60 |
| cttcacagc actgaccatg ttggccctat ttctcccctg cttgcttgct tttctatttt | 120 |
| attttattat tacatttta ttgttagaga gagggtctca ttctgtcgcc caggctggag | 180 |
| tgcagtggca aagtggtgag atctcggctc actgcaacct ccacttgcct cagtctccca | 240 |
| agtagctggg attacaggag cctgacacca tgcccgggta attttgtat ttttgtagag | 300 |
| acggggtttc accatattgg cttgaactcc tgatctcagg tgatccccc accttggcct | 360 |
| cccaaagtgc tgggattaca ggcatgagcc actgcggtgg cctctcccct gctttcaaga | 420 |
| tgccatgctc tcaggggtcc cctccctctt tctccatttc cctggcaaag ttcctcctct | 480 |
| tccccattc agtgtgtgtt gtgatagggg cagaatcctg tctgcactca cttccttggt | 540 |
| gatctcaccc agtcttgtgg ctttaagtac catccataag ccatcaaccc ccaaatttac | 600 |
| atctccagac cagccttatc ccctgaactc ctaaatgcag tgaggttatt cagcatctcc | 660 |
| acagggagat tgtcaggcat ttccaaccct gtatgcccaa acctcgtcac tttccccgca | 720 |
| aacccacttc cctacctttc atctctgcca gcagacactc ccatcttctc agcgtttcat | 780 |
| gccagaaggc ttggctgtct aggatccctc tcaaacacac ccacattcat ttaatcagca | 840 |
| aattttcttg gccctacctc caaaatattt ccagatctcc ctagcctgca caccttgcc | 900 |
| acctgtcatt cccacttgga ccaggccagc agcctccctg gtctctctga ccctcccct | 960 |
| gagttcgttc accaaaggca gtaacggaga cacccctca acacacacag gaagcagatg | 1020 |
| gccttgacac cagcagggtg acatccgcta ttgctactc tctgctcccc cacagttcct | 1080 |
| ctggacttct ctggaccaca gtcctctgcc agacccctgc cagaccccag tccaccatga | 1140 |
| tccatctggg tcacatcctc ttcctgcttt tgctcccagg tgaagccagt ggttacaggg | 1200 |
| gatggtaggc agagcgtttg tgagatgggt gcttgggtga cgtctgcagg gacgggtgat | 1260 |
| gaaagtgggg ttcttctccc tgcacccctt cccttctggg agatccattc tgcttcaggg | 1320 |
| cctgggtcct tgggggcgga aggggtgag acagggagtt ctgagggggc tgcctgttag | 1380 |
| cgtccccttc tcatggctgg gtctctgctg ccacttccaa tttccttgtca ctctccatgt | 1440 |

```
ctctgggagt cccettccca tgtggtcctg ttccatctct ccagcctgga gattacttct      1500
caggacacta cctttccttc tctacaccct attttttggt ttgtttattt tgagatgggg      1560
tcttgctctg ttgtccaggc tggagtgcag tggcacaatc acggctcacg gcagccttga      1620
cttcctgggc tcaggtgatc ctcccagctc agcctcccga gtaactggga ttacaggtgt      1680
gaaccaacac ttccagctaa ttttgtatt tcttgtagag acgaggtctc actatgttgc       1740
ccaggctggt ctcgaactcc tgggctcaag cgatcttcct gcctcggcct cccaaagtgc      1800
tgggatgaca ggcgtgagcc acggtgccag gctgagcatt ctgttttgtg gaccttctct      1860
ccaccctcat ccaccttctt tctctttcca cagtggctgc agctcagacg actccaggag      1920
agagatcatc actccctgcc ttttaccctg gcacttcagg tatcacttcc accccagaag      1980
cttggccaga ggctcccaga acaccccagt ggttctccag gtcaccatcc cacctcccgt      2040
cccaaaatca gaggatccgt gtccttctcc gagtcccaga atcagcgacc ccagcctgt      2100 gttcaggagc acccgtgtg cccgccgcac agccccgagg gtcctgggac accccagcct      2160
ctctgcatct gtctcccgtt tcattcccca agcgcaactc caaggaacct gggacccgcc      2220
ccctcgcagg ggacttcctc tctgcctgtg gccaaagcac agcccagga cgcagagctt      2280 gagttgtctc cctgttccgg cccccactct ccaggctctt gttccggatg tgggtccctc      2340
tctctgccgc tcctggcagg cctcgtggct gctgatgcgg tggcatcgct gctcatcgtg      2400
ggggcggtgt tcctgtgcgc acgcccacgc cgcagcccg cccaaggtga gggcggagat      2460
gggcggggcc tggaaggtgt atagtgtccc taggaggggg gtcccaggga gggggccctt      2520
ggggaagccc tggaggaggt gctggggaaa ccctggggga ggtgcctggg ggaaccctg       2580 aggaaaccc tgaagcaggg ggtccccagg gaagtggaga tatgggtggt caagcttcat       2640
gctttctctc ccctatcccc agaagatggc aaagtctaca tcaacatgcc aggcaggggc      2700
tgaccctcct gcagcttgga cctttgactt ctgaccctct catcctggat ggtgtgtggt      2760
ggcacaggaa cccccgcccc aacttttgga ttgtaataaa acaattgaaa cacctgtagt      2820
cgtattcttt ctcaaagaac cccagagttc caaagcctc cctcccatga actgtttctg       2880
gatccaaggc cccctcagaa ccccacatg tccccatccc atcagcccaa ggatctggca       2940
taatgttttt gtgcttcatg tttattttag gagagtattg gggagcggtc tggtctctca      3000
```

<210> SEQ ID NO 5
<211> LENGTH: 604
<212> TYPE: DNA
<213> ORGANISM: Homo sapiens

<400> SEQUENCE: 5

```
ccacgcgtcc gcgctgcgcc acatcccacc ggcccttaca ctgtggtgtc cagcagcatc       60
cggcttcatg gggggacttg aaccctgcag caggctcctg ctcctgcctc tcctgctggc      120
tgtaagtggt ctccgtcctg tccaggccca ggcccagagc gattgcagtt gctctacggt      180
gagcccgggc gtgctggcag ggatcgtgat gggagacctg gtgctgacag tgctcattgc      240
cctggccgtg tacttcctgg gccggctggt ccctcggggg cgaggggctg cggaggcagc      300
gacccggaaa cagcgtatca ctgagaccga gtcgccttat caggagctcc agggtcagag      360
gtcggatgtc tacagcgacc tcaacacaca gaggccgtat tacaaatgag cccgaatcat      420
gacagtcagc aacatgatac ctggatccag ccattcctga gcccaccct gcacctcatt      480 ccaactccta ccgcgataca gacccacaga gtgccatccc tgagagacca gaccgctccc      540
caatactctc ctaaaataaa catgaagcac aaaaaaaaaa aaaaaaaaa aaaaaaaaa       600
```

| | |
|---|---:|
| aaaa | 604 |

<210> SEQ ID NO 6
<211> LENGTH: 1677
<212> TYPE: DNA
<213> ORGANISM: Homo sapiens

<400> SEQUENCE: 6

| | |
|---|---:|
| gtcctccact tcctggggag gtagctgcag aataaaacca gcagagactc cttttctcct | 60 |
| aaccgtcccg gccaccgctg cctcagcctc tgcctcccag cctctttctg agggaaagga | 120 |
| caagatgaag tggaaggcgc ttttcaccgc ggccatcctg caggcacagt tgccgattac | 180 |
| agaggcacag agctttggcc tgctggatcc caaactctgc tacctgctgg atggaatcct | 240 |
| cttcatctat ggtgtcattc tcactgcctt gttcctgaga gtgaagttca gcaggagcgc | 300 |
| agacgccccc gcgtaccagc agggccagaa ccagctctat aacgagctca atctaggacg | 360 |
| aagagaggag tacgatgttt tggacaagag acgtggccgg gaccctgaga tgggggaaa | 420 |
| gccgcagaga aggaagaacc tcaggaagg cctgtacaat gaactgcaga agataagat | 480 |
| ggcggaggcc tacagtgaga ttgggatgaa aggcgagcgc ggaggggca aggggcacga | 540 |
| tggcctttac cagggtctca gtacagccac caaggacacc tacgacgccc ttcacatgca | 600 |
| ggccctgccc cctcgctaac agccagggga tttcaccact caaaggccag acctgcagac | 660 |
| gcccagatta tgagacacag gatgaagcat ttacaacccg gttcactctt ctcagccact | 720 |
| gaagtattcc cctttatgta caggatgctt tggttatatt tagctccaaa ccttcacaca | 780 |
| cagactgttg tccctgcact cttaaggga gtgtactccc agggcttacg ccctggcct | 840 |
| tgggccctct ggtttgccgg tggtgcaggt agacctgtct cctggcggtt cctcgttctc | 900 |
| cctgggaggc gggcgcactg cctctcacag ctgagttgtt gagtctgttt tgtaaagtcc | 960 |
| ccagagaaag cgcagatgct agcacatgcc ctaatgtctg tatcactctg tgtctgagtg | 1020 |
| gcttcactcc tgctgtaaat ttggcttctg ttgtcacctt cacctccttt caaggtaact | 1080 |
| gtactgggcc atgttgtgcc tccctggtga gagggccggg cagaggggca gatgaaagg | 1140 |
| agcctaggcc aggtgcaacc agggagctgc aggggcatgg gaaggtgggc gggcagggga | 1200 |
| gggtcagcca gggcctgcga gggcagcggg agcctccctg cctcaggcct ctgtgccgca | 1260 |
| ccattgaact gtaccatgtg ctacaggggc cagaagatga acagactgac cttgatgagc | 1320 |
| tgtgcacaaa gtggcataaa aaacatgtgg ttacacagtg tgaataaagt gctgcggagc | 1380 |
| aagaggaggc cgttgattca cttcacgctt tcagcgaatg acaaaatcat ctttgtgaag | 1440 |
| gcctcgcagg aagacccaac acatgggacc tataactgcc cagcggacag tggcaggaca | 1500 |
| ggaaaaaccc gtcaatgtac taggatactg ctgcgtcatt acagggcaca ggccatggat | 1560 |
| ggaaaacgct ctctgctctg cttttttct actgttttaa tttatactgg catgctaaag | 1620 |
| ccttcctatt ttgcataata aatgcttcag tgaaaaaaaa aaaaaaaaa aaaaaa | 1677 |

<210> SEQ ID NO 7
<211> LENGTH: 591
<212> TYPE: DNA
<213> ORGANISM: Homo sapiens

<400> SEQUENCE: 7

| | |
|---|---:|
| cagaacggcc gatctccagc ccaagatgat tccagcagtg gtcttgctct tactccttt | 60 |
| ggttgaacaa gcagcggccc tgggagagcc tcagctctgc tatatcctgg atgccatcct | 120 |
| gtttctgtat ggaattgtcc tcaccctcct ctactgtcga ctgaagatcc aagtgcgaaa | 180 |

```
ggcagctata accagctatg agaaatcaga tggtgtttac acgggcctga gcaccaggaa    240
ccaggagact tacgagactc tgaagcatga gaaaccacca cagtagcttt agaatagatg    300
cggtcatatt cttctttggc ttctggttct tccagccctc atggttggca tcacatatgc    360
ctgcatgcca ttaacaccag ctggccctac ccctataatg atcctgtgtc ctaaattaat    420
atacaccagt ggttcctcct ccctgttaaa gactaatgct cagatgctgt ttacggatat    480
ttatattcta gtctcactct cttgtcccac ccttcttctc ttccccattc ccaactccag    540
ctaaaatatg ggaagggaga accccaata aaactgccat ggactggact c              591
```

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 8

```
gcgaattcgc caccatggca ttgattcgtg atcga                                35
```

<210> SEQ ID NO 9
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 9

```
ggcgctcgag ttacaccgcc cttttcatgc agat                                 34
```

<210> SEQ ID NO 10
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 10

```
ggcgaattcg cattgattcg tgatcgaaag tct                                  33
```

<210> SEQ ID NO 11
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 11

```
gcaagtcgac gccaccatgg accccccagg ctacc                                35
```

<210> SEQ ID NO 12
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 12

```
ggcgaattct cagcctctgc caggcatgtt gat                                  33
```

<210> SEQ ID NO 13
<211> LENGTH: 34
<212> TYPE: DNA
<213> ORGANISM: Artificial Sequence

```
<220> FEATURE:
<223> OTHER INFORMATION: Synthetic oligonucleotide

<400> SEQUENCE: 13
ggcagaattc gcctctgcca ggcatgttga tgta                              34

<210> SEQ ID NO 14
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 14
gttagaattc gccaccatgg gggctctgga gccct                             35

<210> SEQ ID NO 15
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 15
gcaactcgag tcatctgtaa tattgcctct gtg                               33

<210> SEQ ID NO 16
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 16
ggcgtcgaca ccatgagagc aaaattcagc aggag                             35

<210> SEQ ID NO 17
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 17
gcttgaattc gcgaggggcc agggtctgca tat                               33

<210> SEQ ID NO 18
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 18
gcagaattca gagcaaaatt cagcaggagt gc                                32

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 19
gctttctcga gttagcgagg ggccagggtc tgcat                             35
```

```
<210> SEQ ID NO 20
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 20
gcatgtcgac gccaccatgg ccaaggcagc agtga                              35

<210> SEQ ID NO 21
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 21
gcggctcgag tcacatcgca aatgcaaatg c                                  31

<210> SEQ ID NO 22
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 22
gttagaattc gccaccatgg caaagggagc cacc                               34

<210> SEQ ID NO 23
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 23
gcgctcgagt catttttct tcagcataca ccaag                               35
```